US011389284B2

(12) United States Patent
Lenneman et al.

(10) Patent No.: US 11,389,284 B2
(45) Date of Patent: Jul. 19, 2022

(54) EMBOLIC PROTECTION DEVICES

(71) Applicants: BOSTON SCIENTIFIC SCIMED, INC., Maple Grove, MN (US); REGENTS OF THE UNIVERSITY OF MINNESOTA, Minneapolis, MN (US)

(72) Inventors: Tina Marie Lenneman, Otsego, MN (US); Dennis A. Boismier, Shorewood, MN (US); Kyle Harish Srivastava, Saint Paul, MN (US); Kevin J. Goodwin, Minneapolis, MN (US); Felix Landaeta, Minneapolis, MN (US); Paige V. Tracy, South St. Paul, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 194 days.

(21) Appl. No.: 16/586,886

(22) Filed: Sep. 27, 2019

(65) Prior Publication Data

US 2020/0100886 A1 Apr. 2, 2020

Related U.S. Application Data

(60) Provisional application No. 62/738,486, filed on Sep. 28, 2018.

(51) Int. Cl.
*A61F 2/01* (2006.01)
(52) U.S. Cl.
CPC ............. *A61F 2/0105* (2020.05); *A61F 2/011* (2020.05); *A61F 2002/016* (2013.01); *A61F 2230/0069* (2013.01)

(58) Field of Classification Search
CPC .......... A61F 2/01; A61F 2/012; A61F 2/0105; A61F 2/0108
See application file for complete search history.

(56) References Cited

U.S. PATENT DOCUMENTS

| | | | |
|---|---|---|---|
| 5,814,064 A | 9/1998 | Daniel et al. | |
| 6,168,604 B1 * | 1/2001 | Cano ...................... | A61F 2/013 606/114 |
| 7,094,249 B1 | 8/2006 | Broome et al. | |
| 8,372,108 B2 | 2/2013 | Lashinski | |
| 8,728,114 B2 | 5/2014 | Belson | |
| 8,753,370 B2 | 6/2014 | Lashinski | |
| 9,017,364 B2 | 4/2015 | Fifer et al. | |
| 9,107,734 B2 | 8/2015 | Belson | |
| 9,119,706 B2 | 9/2015 | Daniel et al. | |
| 9,339,367 B2 | 5/2016 | Carpenter et al. | |
| 2002/0010411 A1 * | 1/2002 | Macoviak ........... | A61M 1/3613 604/8 |
| 2002/0143362 A1 | 10/2002 | Macoviak et al. | |
| 2003/0105486 A1 | 6/2003 | Murphy et al. | |

(Continued)

*Primary Examiner* — Tuan V Nguyen
(74) *Attorney, Agent, or Firm* — Seager, Tufte & Wickhem, LLP

(57) ABSTRACT

Embolic protection devices and methods for making and using embolic protection devices are disclosed. An embolic protection device may include an elongate filter wire having a distal end region, a filter anchor coupled to the distal end region, a filter membrane coupled to the filter anchor, and a bumper coupled to the filter anchor. The bumper may be designed to provide a tactile feedback to a clinician during delivery of the embolic protection device.

10 Claims, 12 Drawing Sheets

(56) References Cited

U.S. PATENT DOCUMENTS

| | | | |
|---|---|---|---|
| 2004/0097805 A1* | 5/2004 | Verard | A61B 1/00071 600/428 |
| 2006/0122522 A1* | 6/2006 | Chavan | A61B 5/6862 600/505 |
| 2009/0254172 A1* | 10/2009 | Grewe | A61F 2/86 623/1.15 |
| 2012/0296262 A1* | 11/2012 | Ogata | A61M 25/09 604/20 |
| 2014/0039544 A1 | 2/2014 | Bergheim | |
| 2014/0100597 A1 | 4/2014 | Wang et al. | |
| 2014/0249567 A1* | 9/2014 | Adams | A61F 2/01 606/200 |
| 2014/0330305 A1* | 11/2014 | Rood | A61F 2/01 606/200 |
| 2015/0182324 A1 | 7/2015 | Naor et al. | |
| 2016/0262864 A1* | 9/2016 | Von Mangoldt | A61F 2/01 |
| 2017/0224354 A1 | 8/2017 | Tischler et al. | |

\* cited by examiner

EMBOLIC PROTECTION DEVICES

CROSS-REFERENCE TO RELATED APPLICATIONS

This application claims the benefit of priority under 35 U.S.C. § 119 to U.S. Provisional Application Ser. No. 62/738,486, filed Sep. 28, 2018, the entirety of which is incorporated herein by reference.

TECHNICAL FIELD

The present disclosure pertains to medical devices, and methods for manufacturing medical devices. More particularly, the present disclosure pertains to embolic protection devices.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example embolic protection device is disclosed. The embolic protection device comprises: an elongate filter wire having a distal end region; a filter anchor coupled to the distal end region; a filter membrane coupled to the filter anchor; and a bumper coupled to the filter anchor, the bumper being designed to provide a tactile feedback to a clinician during delivery of the embolic protection device.

Alternatively or additionally to any of the embodiments above, the filter anchor includes a hoop.

Alternatively or additionally to any of the embodiments above, the filter anchor includes a stent-like structure.

Alternatively or additionally to any of the embodiments above, the filter membrane includes a mesh.

Alternatively or additionally to any of the embodiments above, the filter membrane includes a sac.

Alternatively or additionally to any of the embodiments above, the bumper includes a woven disk.

Alternatively or additionally to any of the embodiments above, further comprising an ultrasound-visible coating disposed along at least a portion of the filter wire, the filter anchor, the filter membrane, the bumper, or combinations thereof.

Alternatively or additionally to any of the embodiments above, further comprising a sensor coupled to at least one of the filter wire, the filter anchor, the filter membrane, or the bumper.

Alternatively or additionally to any of the embodiments above, the sensor includes an impedance sensor.

Alternatively or additionally to any of the embodiments above, the sensor includes a flow sensor.

Alternatively or additionally to any of the embodiments above, the sensor includes a pressure sensor.

An embolic protection device is disclosed. The embolic protection device comprises: a filter anchor; a filter membrane disposed adjacent to the filter anchor; and a sensor disposed adjacent to the filter anchor, the sensor being designed to provide a location indication to a clinician during delivery of the embolic protection device.

Alternatively or additionally to any of the embodiments above, the filter anchor includes a hoop.

Alternatively or additionally to any of the embodiments above, the filter anchor includes a stent-like structure.

Alternatively or additionally to any of the embodiments above, the filter membrane includes a mesh.

Alternatively or additionally to any of the embodiments above, further comprising an ultrasound-visible coating disposed along at least a portion of the filter wire, the filter anchor, the filter membrane, or combinations thereof.

Alternatively or additionally to any of the embodiments above, the sensor includes an impedance sensor.

Alternatively or additionally to any of the embodiments above, the sensor includes a flow sensor.

Alternatively or additionally to any of the embodiments above, the sensor includes a pressure sensor.

A method for placing an embolic protection device at least partially along an aorta without the use of fluoroscopy is disclosed. The method comprises: advancing an embolic protection device through a blood vessel to a position adjacent to an aorta, the embolic protection device comprising: a filter anchor, a filter membrane disposed adjacent to the filter anchor, and a sensor disposed adjacent to the filter anchor, the sensor being designed to provide a location indication to a clinician during delivery of the embolic protection device; and sensing with the sensor to determine the location of the embolic protection device.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
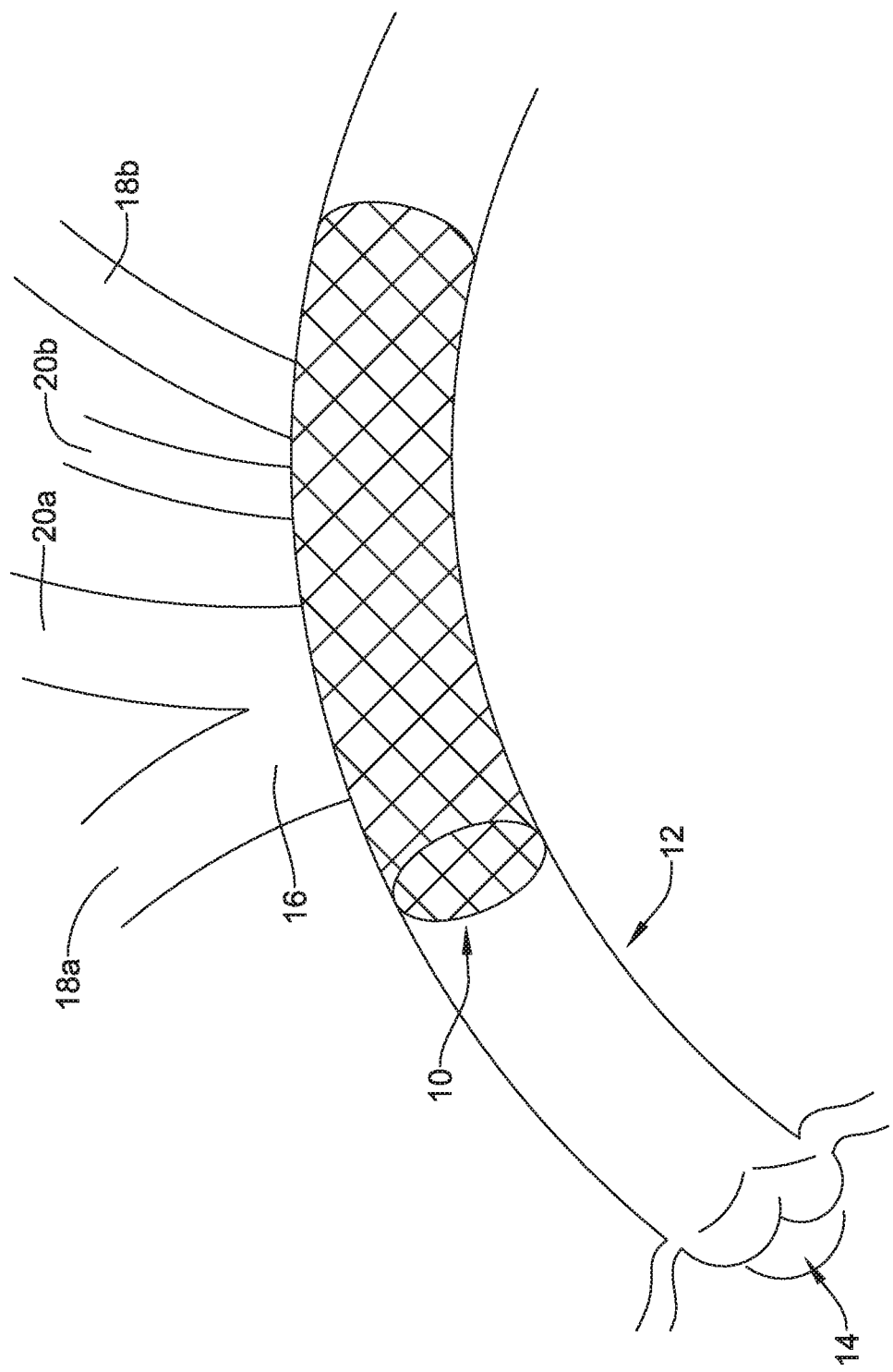
FIG. 1 is a plan view of an example embolic protection device disposed in a blood vessel.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

A number of medical interventions may result in embolic material being released into the blood stream as part of the procedure. For a number of reasons, it may be desirable to limit the amount of embolic material released, contain embolic material, direct any released embolic material away from sensitive body regions, and/or combinations thereof. Disclosed herein are embolic protection devices that are designed to provide some of these and other features.

FIG. 1 is a plan view of an example embolic protection device 10 disposed in an aorta 12. In this example, the aortic valve 14, brachiocephalic trunk 16, right subclavian artery 18a, left subclavian artery 18b, right common carotid artery 20a, and left common carotid artery 20b are schematically shown. During some interventions such as transcatheter aortic valve replacement and/or other cardiac interventions, embolic material could be released into the vasculature. For a number of reasons, it may be desirable to contain the embolic material and/or shield at least portions of the vasculature from the embolic material. This may include limiting the access of the embolic material to the brachiocephalic trunk 16, right subclavian artery 18a, left subclavian artery 18b, right common carotid artery 20a, and/or left common carotid artery 20b.

Figure 2:
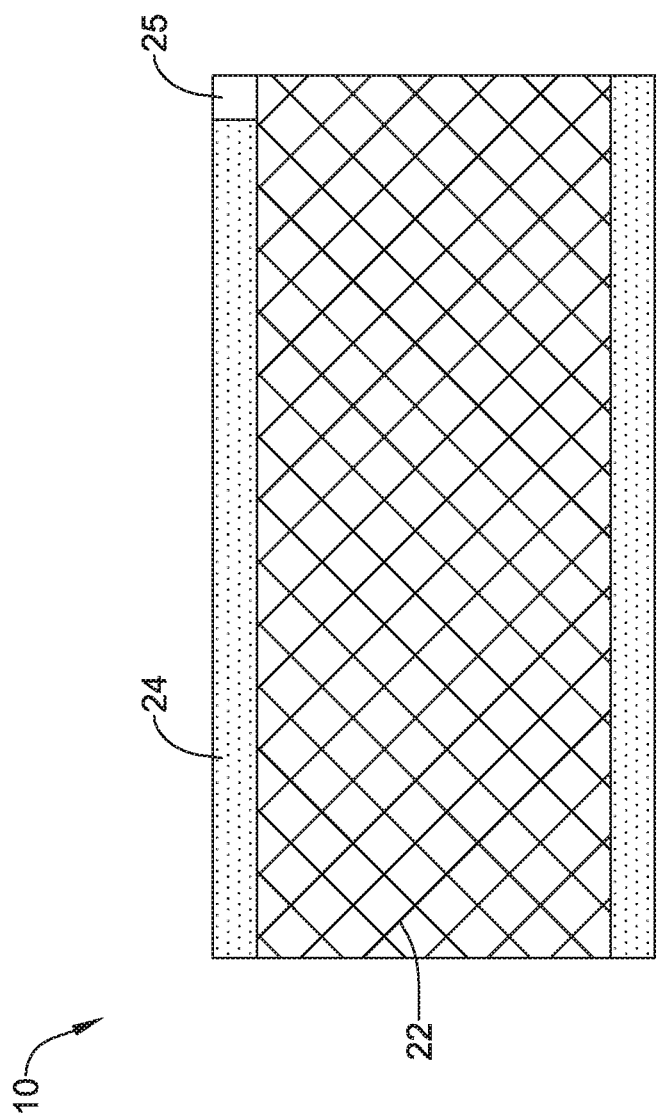
FIG. 2 is a side view of an example embolic protection device.

FIG. 2 is a side view of the embolic protection device 10. Here it can be seen that the embolic protection device 10 may include a stent or anchor 22. The anchor 22 is generally designed to be disposed within the aorta 12. A membrane 24 may be disposed along the anchor 22. The membrane 24 may be permeable to blood (e.g., which may include cells, blood components, and the like) while being resistant to the passing of embolic material. Thus, when the anchor 22 is disposed along the aortic arch, the anchor 22 may overlie one or more of the brachiocephalic trunk 16, right subclavian artery 18a, left subclavian artery 18b, right common carotid artery 20a, and left common carotid artery 20b. The membrane 24 may serve to shield these vessels from any released embolic material that may pass through the aorta 12.

As will be discussed herein, the embolic protection device 10 may be delivered using a catheter system or the like. Some cardiac interventions that may have a propensity to result in the release of embolic material may be performed in a surgical suite rather than a "catheter lab" or angiogram/angioplasty lab. Because catheter labs typically include fluoroscopy imaging capital equipment that allow for imaging of the catheter and/or medical device during the intervention, precise delivery of a medical device is possible using the available imaging systems. A surgical suite, in contrast, is not typically equipped with such imaging systems. Thus, it may be challenging to deliver a medical device under these circumstances with the precision typically achieved in a catheter lab under fluoroscopic guidance.

The embolic protection device 10 may include one more features that allow the device 10 to be imaged in a surgical suite and/or in an environment where fluoroscopic imaging equipment is not always present. For example, in some instances, the embolic protection device 10 may include a radiopaque material. For example, the anchor 22, the membrane 24, or combinations thereof may include a radiopaque marker, coil, filler, or the like. In some of these and in other instances, the anchor 22, the membrane 24, or combinations thereof may include a coating or otherwise incorporate a material that is imagable or otherwise visible to ultrasound (e.g., using external ultrasound, transesophageal ultrasound, or the like). For example, the anchor 22, the membrane 24, or combinations thereof may include a region with an ultrasound-sensitive coating or material.

In some of these and in other instances, the embolic protection device 10 may include one or more sensors 25. In FIG. 2, the sensor(s) 25 are schematically depicted and, as shown, the sensor 25 may be a part of or incorporated into the anchor 22, the sensor 25 may be a part of or incorporated into the membrane 24, and/or combinations thereof. In general, the sensor 25 may be used to help identify the location of the embolic protection device 10 during and after delivery. The sensor 25 may be compatible with one or more pieces of imaging hardware such as those typically found in a surgical suite. In some instances, the sensor 25 may be an impedance sensor. For example, an impedance sensor could be tuned to identify the aortic arch as a suitable location for delivery of the embolic protection device 10 as opposed to right subclavian artery 18a or other arteries. The impedance sensor could send or generate a signal that can be detected using a controller or processor that is coupled to the embolic protection device 10 and/or a delivery catheter used to deliver the embolic protection device 10.

In other instances, the sensor 25 may be a flow sensor. A flow sensor could be tuned to identify the flow in the aortic arch as a suitable location as opposed to right subclavian artery 18a or other arteries. The flow sensor could send or generate a signal that can be detected using a controller or processor that is coupled to the embolic protection device 10 and/or a delivery catheter used to deliver the embolic protection device 10. For example, the flow sensor may be able to detect blood flow indicative of the sensor being disposed in the aorta.

In other instances, the sensor 25 may be a pressure sensor. A pressure sensor could be tuned to identify the average or peak systolic pressure in the aortic arch as a suitable location as opposed to the right subclavian artery 18a or other arteries. The pressure sensor could send or generate a signal that can be detected using a controller or processor that is coupled to the embolic protection device 10 and/or a delivery catheter used to deliver the embolic protection device 10. For example, the pressure sensor may be able to detect pressure (e.g., blood pressure) indicative of the sensor being disposed in the aorta.

Figure 3:
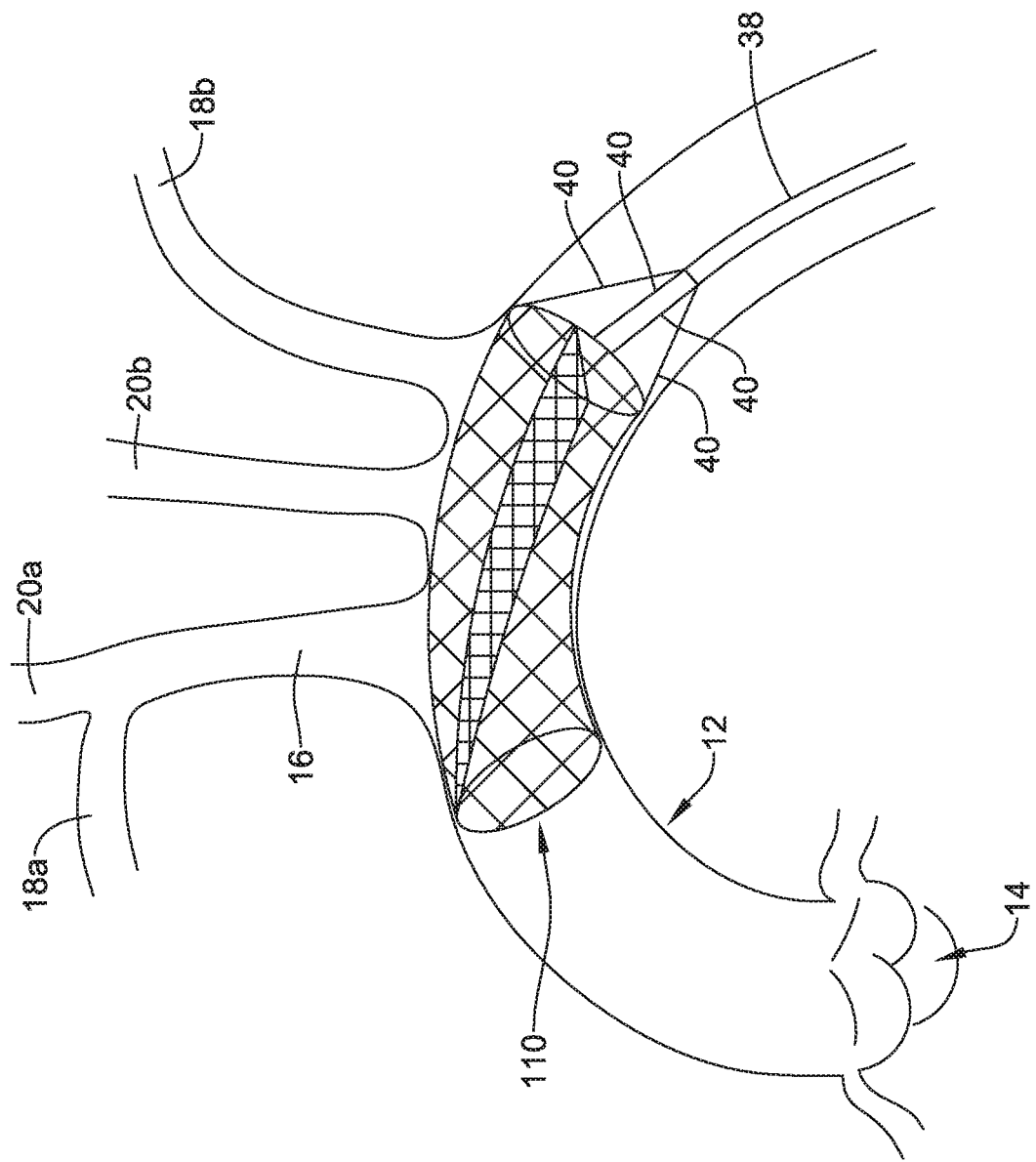
FIG. 3 is a plan view of an example embolic protection device disposed in a blood vessel.
Figure 4:
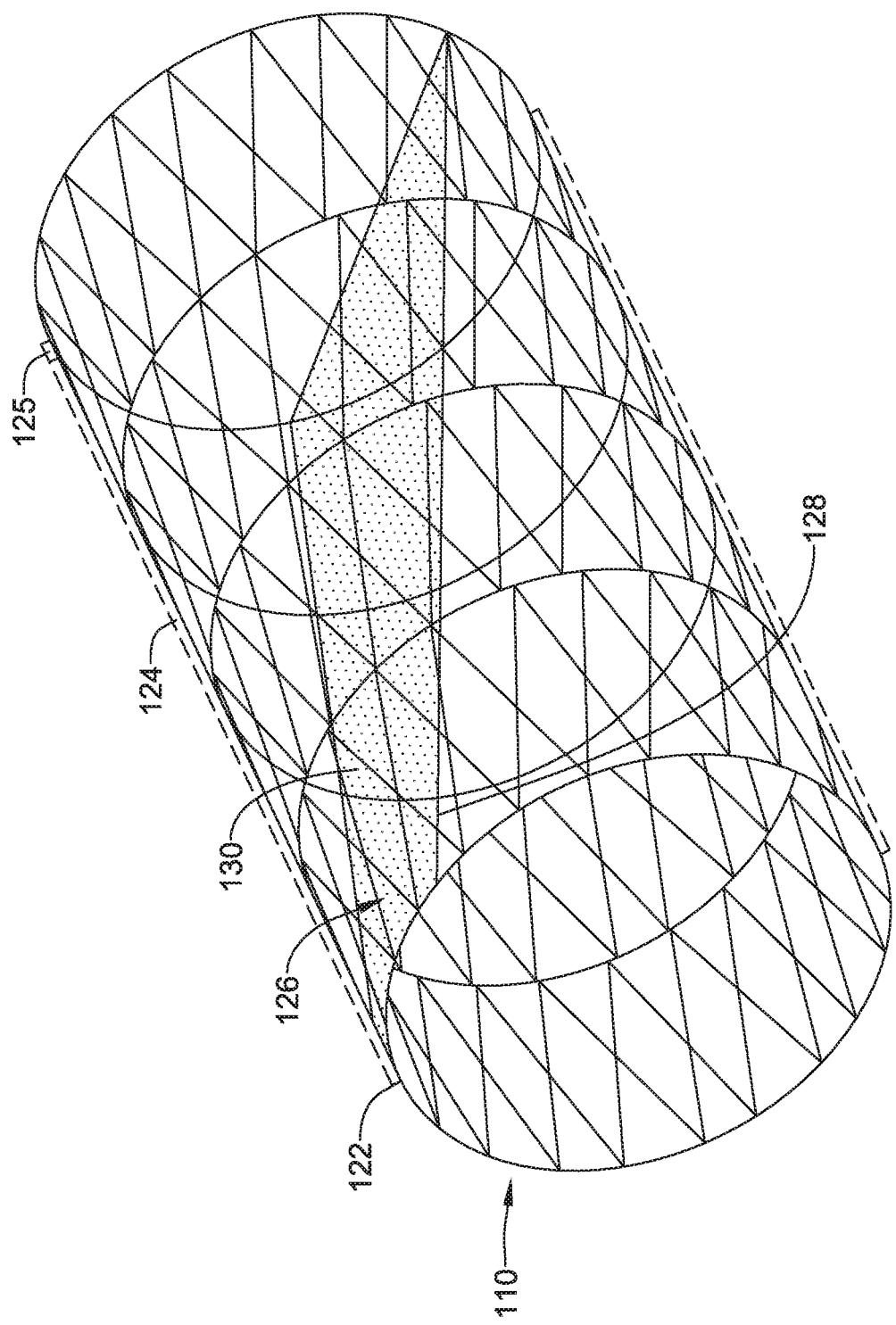
FIG. 4 is a side view of an example embolic protection device.

FIGS. 3-4 depict another example embolic protection device 110, which may be similar in form and function to other embolic protection devices disclosed herein. The embolic protection device 110 may include a stent or anchor 122. Optionally, a membrane 124 may be disposed along the anchor 122. The membrane 124 may be permeable to blood (e.g., which may include cells, blood components, and the like) while being resistant to the passing of embolic material. The embolic protection device 110 may include a ramp member 126. The ramp member 126 may include a frame 128 and a membrane 130. The membrane 130 may be permeable to blood (e.g., which may include cells, blood components, and the like) while being resistant to the passing of embolic material. Thus, the ramp member 126 may help to prevent embolic material from passing therethrough (e.g., the membrane 24 may serve to shield the brachiocephalic trunk 16, right subclavian artery 18a, left subclavian artery 18b, right common carotid artery 20a, and left common carotid artery 20b from any released embolic material that may pass through the aorta 12). In addition, the ramp member 126 may be angled across the anchor 122 so that any captured embolic material may be diverted away from branch vessels coming off of the aorta 12.

Also depicted in FIG. 3 is a delivery catheter 38 for delivering the embolic protection device 110. The delivery catheter 38, which is shown schematically, may include one or more engagement members or wires 40 coupled to a proximal end region of the embolic protection device 110. In at least some instances, the delivery catheter 38 may be used to delivery and/or retrieve the embolic protection device 110.

Like the embolic protection device 10, the embolic protection device 110 may include one more features that allow the device 110 to be imaged in a surgical suite and/or in an environment where fluoroscopic imaging equipment is not always present. For example, in some instances, the embolic protection device 110 may include a radiopaque material, an ultrasound-sensitive coating or material, or the like. In some of these and in other instances, the embolic protection device 110 may include one or more sensors 125. In FIG. 4, the sensor(s) 125 are schematically depicted and the sensor 125 may be a part of or incorporated into the anchor 122, the sensor 125 may be a part of or incorporated into the membrane 124, and/or combinations thereof. In general, the sensor 125 may be used to help identify the location of the embolic protection device 110 during and after delivery. The sensor 125 may be compatible with one or more pieces of imaging hardware such as those typically found in a surgical suite. In some instances, the sensor 125 may be an impedance sensor, a flow sensor, a pressure sensor, or the like.

Figure 5:
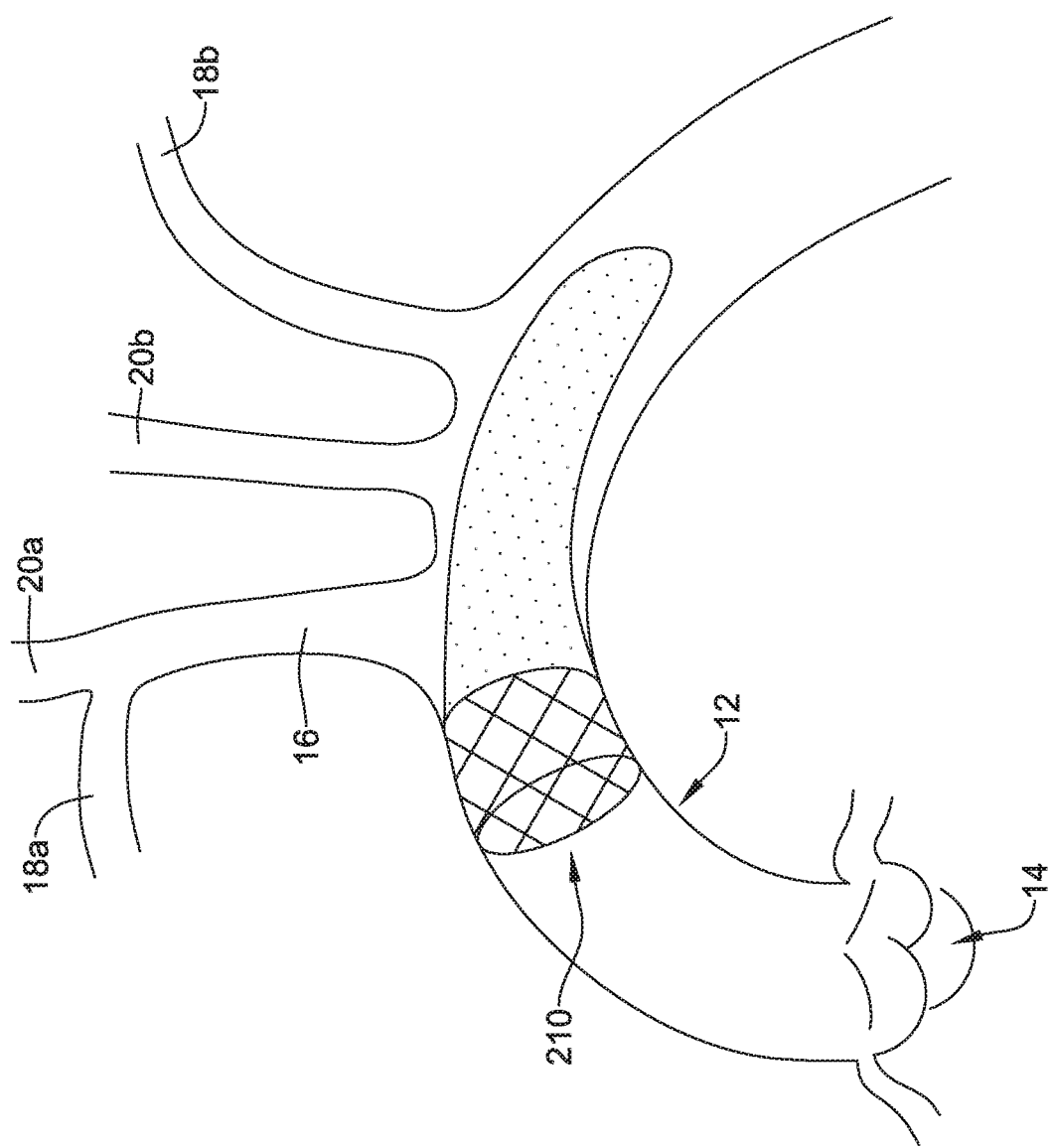
FIG. 5 is a plan view of an example embolic protection device disposed in a blood vessel.
Figure 6:
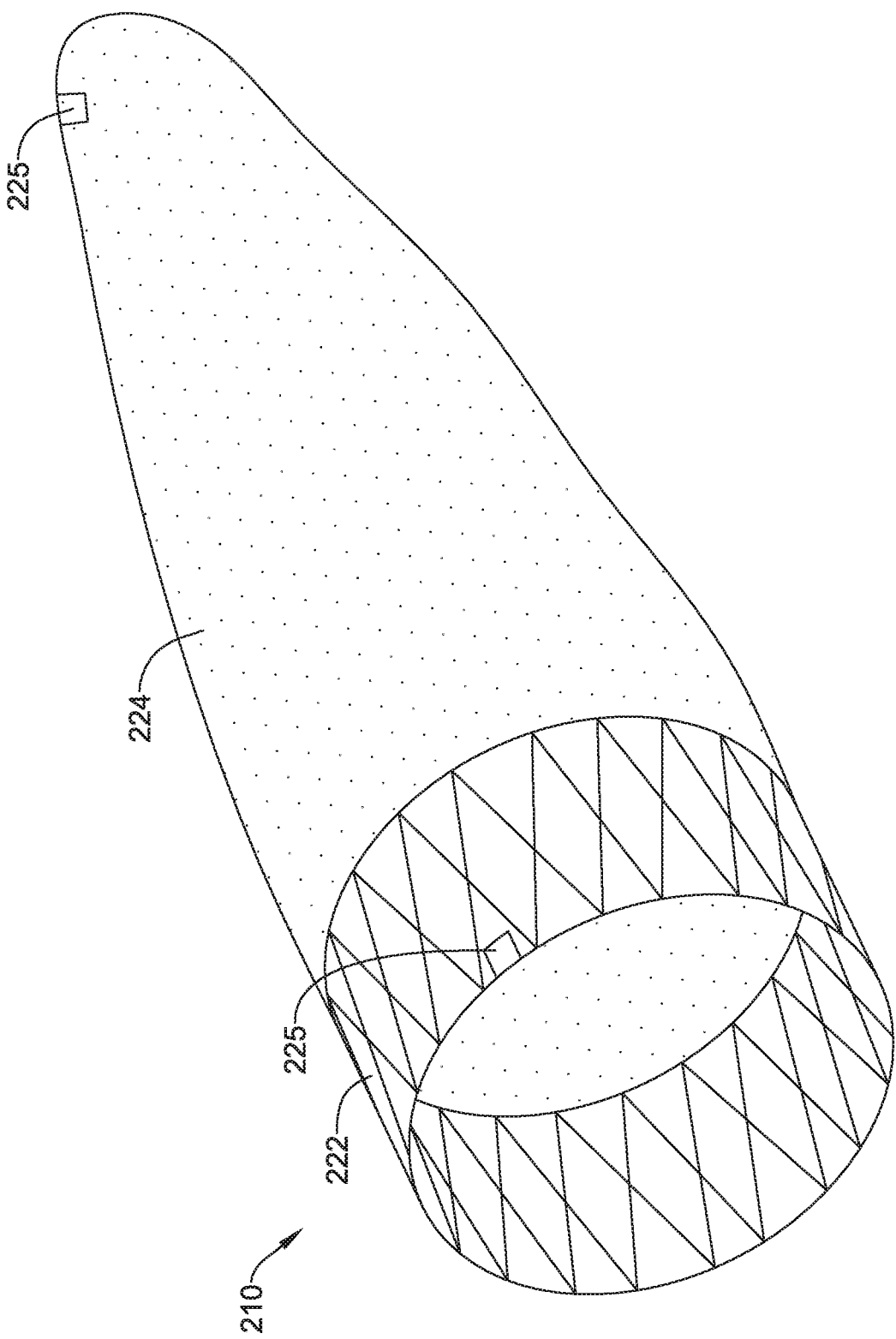
FIG. 6 is a side view of an example embolic protection device.

FIGS. 5-6 depict another example embolic protection device 210, which may be similar in form and function to other embolic protection devices disclosed herein. The embolic protection device 210 may include a stent or anchor 222. A membrane 224 may be disposed along the anchor 222. The membrane 224 may be permeable to blood (e.g., which may include cells, blood components, and the like) while being resistant to the passing of embolic material. In the embolic protection device 210, the anchor 222 may be used to anchor the embolic protection device 210 at a suitable location (e.g., upstream of the brachiocephalic trunk 16, right subclavian artery 18a, left subclavian artery 18b, right common carotid artery 20a, and/or left common carotid artery 20b) and the membrane 224 may take the form of a sac (e.g., which may resemble a windsock) that is secured to the anchor 222 and extends upstream therefrom.

Like the other embolic protection devices disclosed herein, the embolic protection device 210 may include one more features that allow the device 210 to be imaged in a surgical suite and/or in an environment where fluoroscopic imaging equipment is not always present. For example, in some instances, the embolic protection device 210 may include a radiopaque material, an ultrasound-sensitive coating or material, or the like. In some of these and in other instances, the embolic protection device 210 may include one or more sensors 225. In FIG. 6, the sensor(s) 225 are schematically depicted and the sensor 225 may be a part of or incorporated into the anchor 222, the sensor 225 may be a part of or incorporated into the membrane 224, and/or combinations thereof. In general, the sensor 225 may be used to help identify the location of the embolic protection device 210 during and after delivery. The sensor 225 may be compatible with one or more pieces of imaging hardware such as those typically found in a surgical suite. In some instances, the sensor 225 may be an impedance sensor, a flow sensor, a pressure sensor, or the like.

Figure 7:
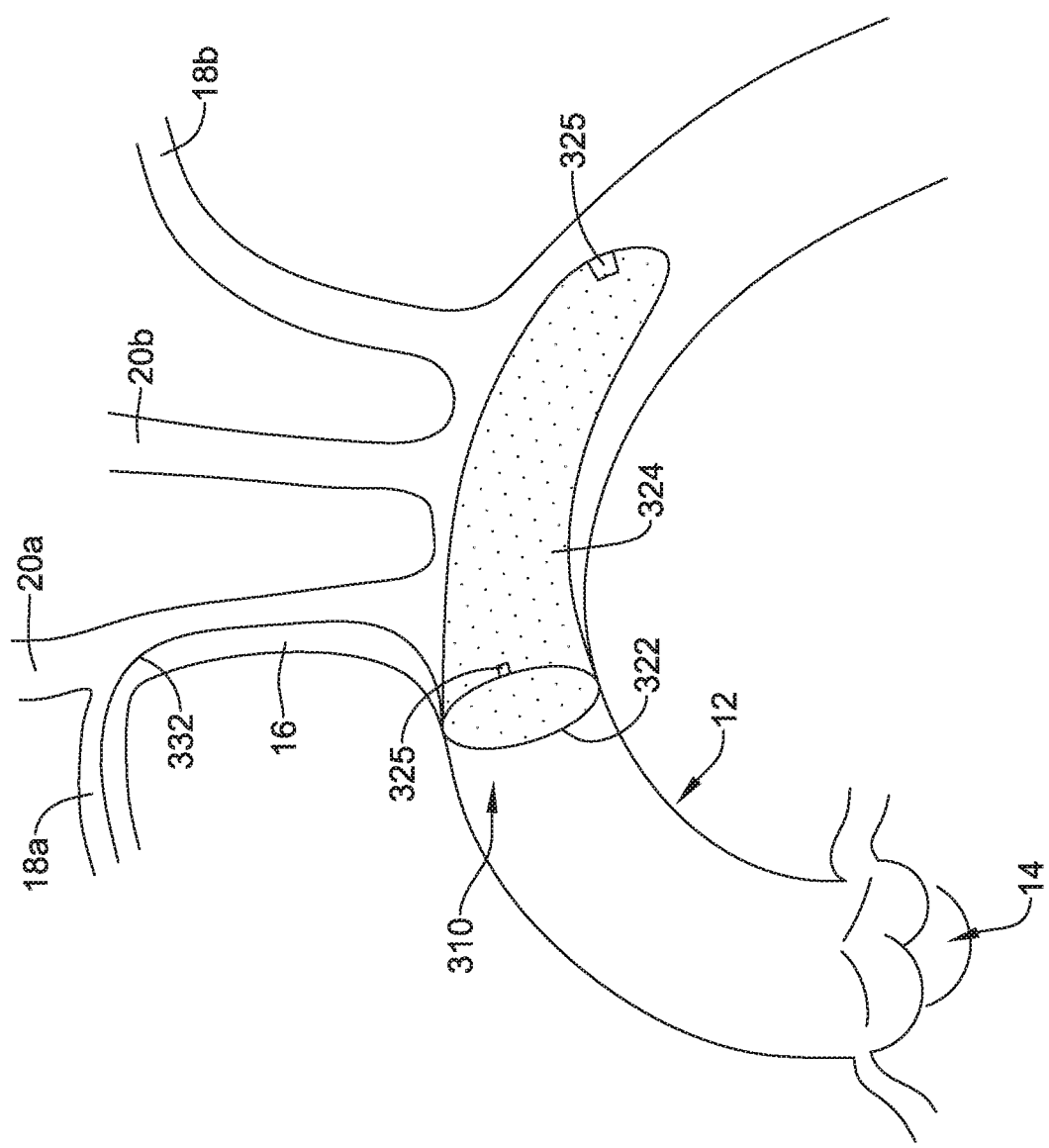
FIG. 7 is a plan view of an example embolic protection device disposed in a blood vessel.

FIG. 7 depicts another example embolic protection device 310, which may be similar in form and function to other embolic protection devices disclosed herein. The embolic protection device 310 may include a stent or anchor 322. A membrane 324 may be disposed along the anchor 322. The membrane 324 may be permeable to blood (e.g., which may include cells, blood components, and the like) while being resistant to the passing of embolic material. In the embolic protection device 310, the anchor 322 may take the form of a loop that can be used anchor the embolic protection device 310 at a suitable location (e.g., upstream of the brachiocephalic trunk 16, right subclavian artery 18a, left subclavian artery 18b, right common carotid artery 20a, and/or left common carotid artery 20b) and the membrane 324 may take the form of a sac (e.g., which may resemble a windsock) that is secured to the anchor 322 and extends downstream therefrom.

Like the other embolic protection devices disclosed herein, the embolic protection device 310 may include one more features that allow the device 310 to be imaged in a surgical suite and/or in an environment where fluoroscopic imaging equipment is not always present. For example, in some instances, the embolic protection device 310 may include a radiopaque material, an ultrasound-sensitive coating or material, or the like. In some of these and in other instances, the embolic protection device 310 may include a sensor 325. In FIG. 7, the sensor(s) 325 are schematically depicted and the sensor 325 may be a part of or incorporated into the anchor 322, the sensor 325 may be a part of or incorporated into the membrane 324, and/or combinations thereof. In general, the sensor 325 may be used to help identify the location of the embolic protection device 310 during and after delivery. The sensor 325 may be compatible with one or more pieces of imaging hardware such as those typically found in a surgical suite. In some instances, the sensor 325 may be an impedance sensor, a flow sensor, a pressure sensor, or the like.

Also shown in FIG. 7 is a delivery member 332. In this example, the delivery member 332 takes the form of a filter wire 332 that may be coupled to the anchor 322. The delivery member 332 may be used to help deliver/position the embolic protection device 310. For example, the delivery member 332 may be used to help navigate the embolic protection device 310 through the right subclavian artery 18a, through the brachiocephalic trunk 16, and into the aorta 12. This may include passing the delivery member 332 (and the embolic protection device 310) through a delivery catheter (not shown).

Figure 8:
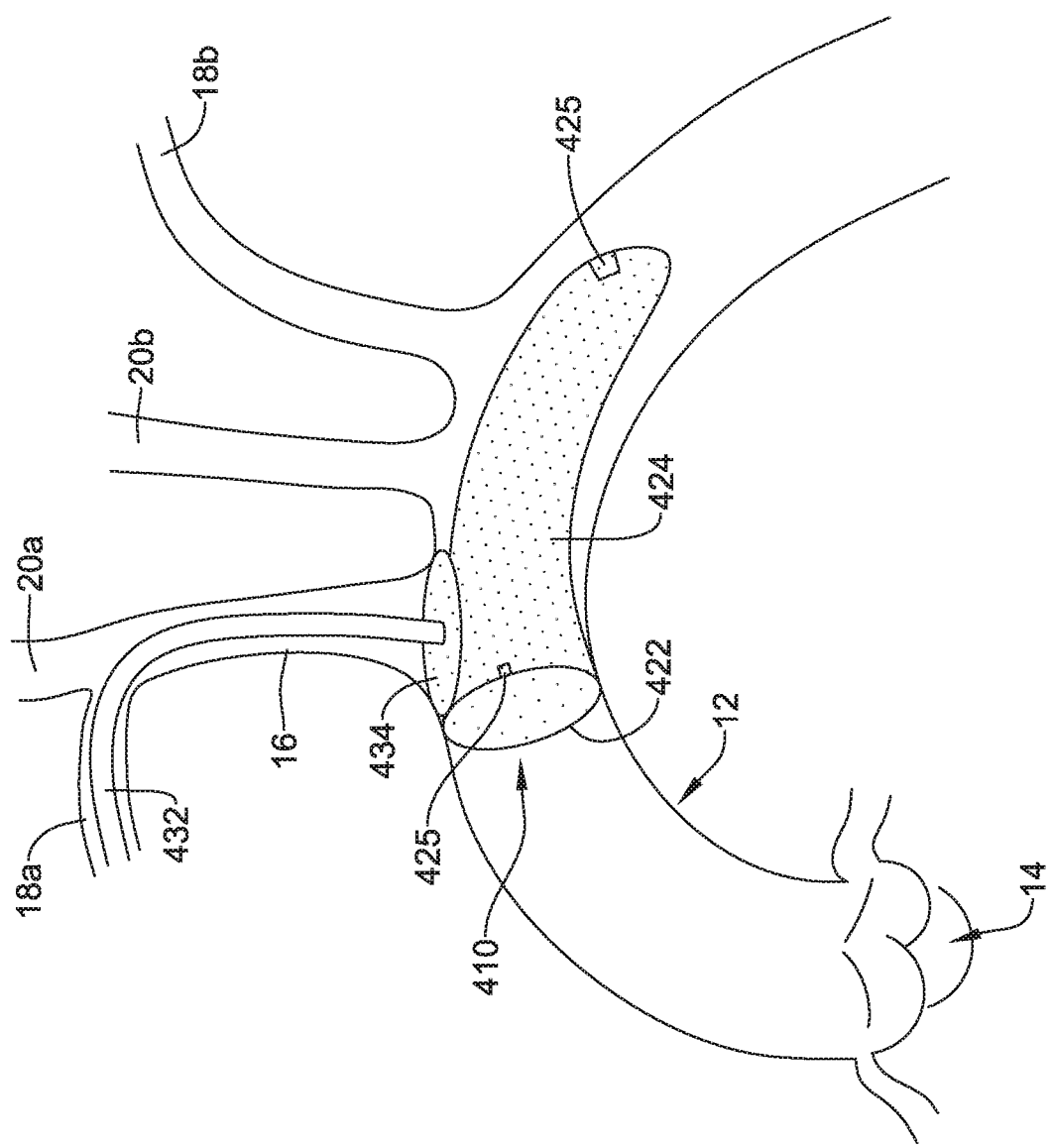
FIG. 8 is a plan view of an example embolic protection device disposed in a blood vessel.

FIG. 8 depicts another example embolic protection device 410, which may be similar in form and function to other embolic protection devices disclosed herein. The embolic protection device 410 may include a stent or anchor 422. A membrane 424 may be disposed along the anchor 422. The membrane 424 may be permeable to blood (e.g., which may include cells, blood components, and the like) while being resistant to the passing of embolic material. In the embolic protection device 410, the anchor 422 may take the form of a loop that can be used anchor the embolic protection device 410 at a suitable location (e.g., upstream of the brachiocephalic trunk 16, right subclavian artery 18a, left subclavian artery 18b, right common carotid artery 20a, and/or left common carotid artery 20b) and the membrane 424 may take the form of a sac (e.g., which may resemble a windsock) that is secured to the anchor 422 and extends upstream therefrom.

Like the other embolic protection devices disclosed herein, the embolic protection device 410 may include one more features that allow the device 410 to be imaged in a surgical suite and/or in an environment where fluoroscopic imaging equipment is not always present. For example, in some instances, the embolic protection device 410 may include a radiopaque material, an ultrasound-sensitive coating or material, or the like. In some of these and in other instances, the embolic protection device 410 may include a sensor 425. In FIG. 8, the sensor(s) 425 are schematically depicted and the sensor 425 may be a part of or incorporated into the anchor 422, the sensor 425 may be a part of or incorporated into the membrane 424, and/or combinations thereof. In general, the sensor 425 may be used to help identify the location of the embolic protection device 410 during and after delivery. The sensor 425 may be compatible with one or more pieces of imaging hardware such as those typically found in a surgical suite. In some instances, the sensor 425 may be an impedance sensor, a flow sensor, a pressure sensor, or the like.

Also shown in FIG. 8 is a delivery member 432. In this example, the delivery member 432 takes the form of a delivery catheter coupled to the embolic protection device 410. The delivery member 432 may be used to help deliver/position the embolic protection device 410. For example, the delivery member 432 may be used to help navigate the embolic protection device 410 through the right subclavian artery 18a, through the brachiocephalic trunk 16, and into the aorta 12. In at least some instances, a filter wire (not shown) may be coupled to the embolic protection device 410 and may extend through the delivery member 432 during delivery.

The embolic protection device 410 may include a bumper 434. The bumper 434 may take the form of a non-woven or woven disk, stent or stent-like structure, or the like. In at least some instances, the bumper 434 may be designed to shift between a first or collapsed configuration and a second or expanded configuration. In FIG. 8, the bumper 434 is depicted in an example "expanded" configuration. In at least some instances, the bumper 434 may be designed to provide a tactile feedback to a clinician during delivery of the embolic protection device 410. For example, the embolic protection device 410 may be advanced into the aorta 12. When doing so, the bumper 434 may also be advanced within the aorta 12. In some instances, the bumper 434 may be in the first configuration when advancing into the aorta 12 and then may shift to the expanded configuration when reaching the aorta 12. When a clinician determines that the embolic protection device 410 is suitably positioned within the aorta 12, the clinician may exert a proximally-directed force onto the filter wire 432. When doing so, the bumper 434 may lodged against the ostium of the brachiocephalic trunk 16 and be resistant to being moved further proximally. The resistance may provide a tactile feedback (e.g., a feeling that the bumper 434 is securely lodged against the anatomy) to the clinician that indicates that the embolic protection device 410 is suitably delivered to a desirable location.

Figure 9:
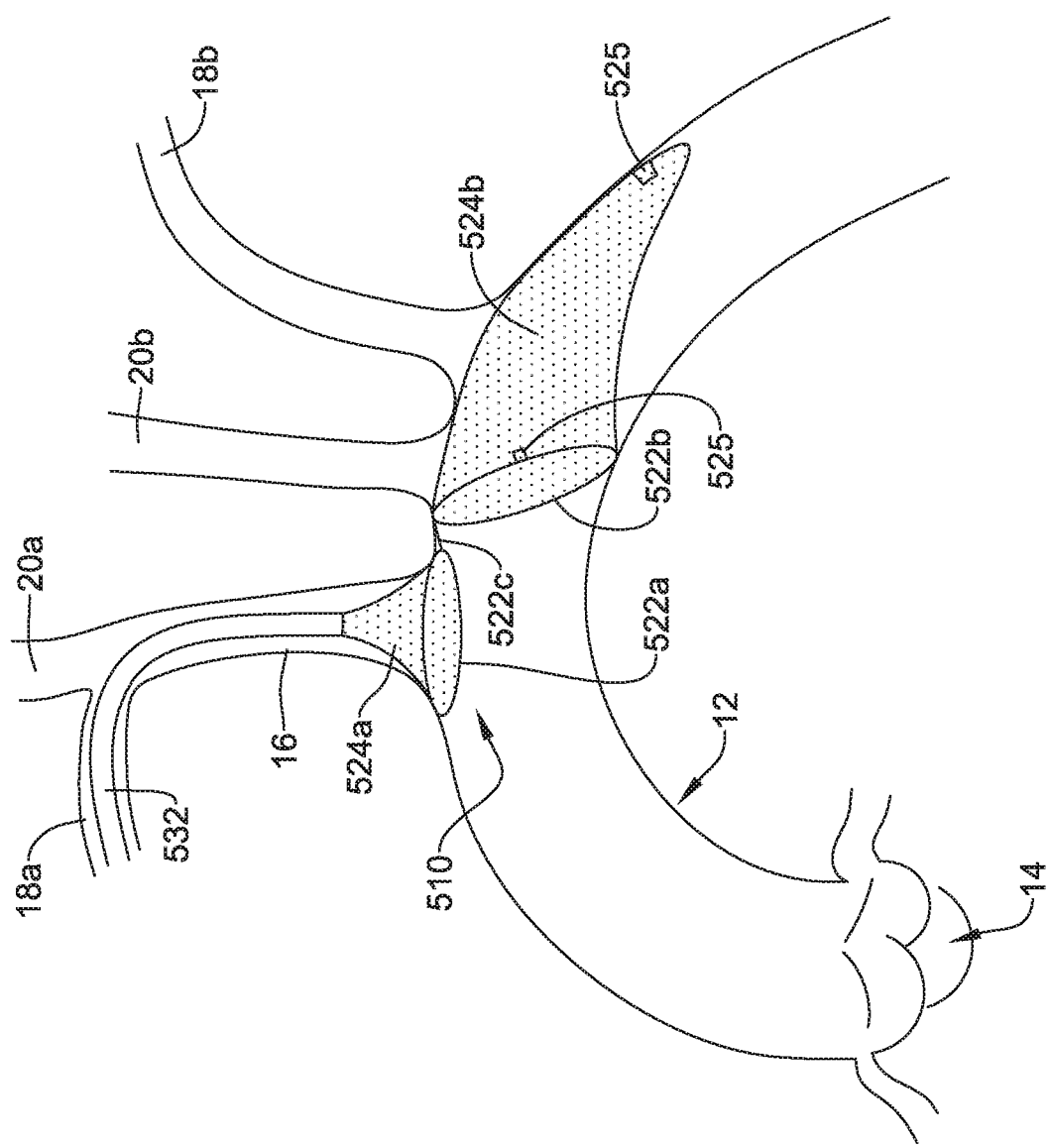
FIG. 9 is a plan view of an example embolic protection device disposed in a blood vessel.

FIG. 9 depicts another example embolic protection device 510, which may be similar in form and function to other embolic protection devices disclosed herein. The embolic protection device 510 may include a first stent or anchor 522a and a second stent or anchor 522b. A first membrane 524a may be coupled to the first anchor 522a. A second membrane 524b may be coupled to the second anchor 522b. A linkage 522c may extend between the first anchor 522a and the second anchor 522b. The first membrane 524a, the second membrane 522b, or both may be permeable to blood (e.g., which may include cells, blood components, and the like) while being resistant to the passing of embolic material.

Like the other embolic protection devices disclosed herein, the embolic protection device 510 may include one more features that allow the device 510 to be imaged in a surgical suite and/or in an environment where fluoroscopic imaging equipment is not always present. For example, in some instances, the embolic protection device 510 may include a radiopaque material, an ultrasound-sensitive coating or material, or the like. In some of these and in other instances, the embolic protection device 510 may include one or more sensors 525. In FIG. 9, the sensor(s) 525 are schematically depicted and the sensor 525 may be a part of or incorporated into the anchor 522a/522b, the sensor 525 may be a part of or incorporated into the membrane 524a/524b, and/or combinations thereof. In general, the sensor 525 may be used to help identify the location of the embolic protection device 510 during and after delivery. The sensor 525 may be compatible with one or more pieces of imaging hardware such as those typically found in a surgical suite. In some instances, the sensor 525 may be an impedance sensor, a flow sensor, a pressure sensor, or the like.

Also shown in FIG. 9 is a delivery member 532. In this example, the delivery member 532 takes the form of a delivery catheter coupled to the embolic protection device 510. The delivery member 532 may be used to help deliver/position the embolic protection device 510. For example, the delivery member 532 may be used to help navigate the embolic protection device 510 through the right subclavian artery 18*a*, through the brachiocephalic trunk 16, and into the aorta 12. In at least some instances, a filter wire (not shown) may be coupled to the embolic protection device 510 and may extend through the delivery member 532 during delivery.

The first anchor 522*a* of the embolic protection device 510 may form or otherwise resemble a bumper (e.g., similar to the bumper 434). In at least some instances, the first anchor/bumper 522*a* may be designed to provide a tactile feedback to a clinician during delivery of the embolic protection device 510. For example, the embolic protection device 510 may be advanced into the aorta 12. When doing so, the first anchor/bumper 522*a* may also be advanced within the aorta 12. In some instances, the first anchor/bumper 522*a* may be in a first or collapsed configuration when advancing into the aorta 12 and then may shift to an expanded configuration when reaching the aorta 12. When a clinician determines that the embolic protection device 510 is suitably positioned within the aorta 12, the clinician may exert a proximally-directed force onto the filter wire 532. When doing so, the first anchor/bumper 522*a* may lodged against the ostium of the brachiocephalic trunk 16 and be resistant to being moved further proximally. The resistance may provide a tactile feedback (e.g., a feeling that the first anchor/bumper 522*a* is securely lodged against the anatomy) to the clinician that indicates that the embolic protection device 510 is suitably delivered to a desirable location.

Figure 10:
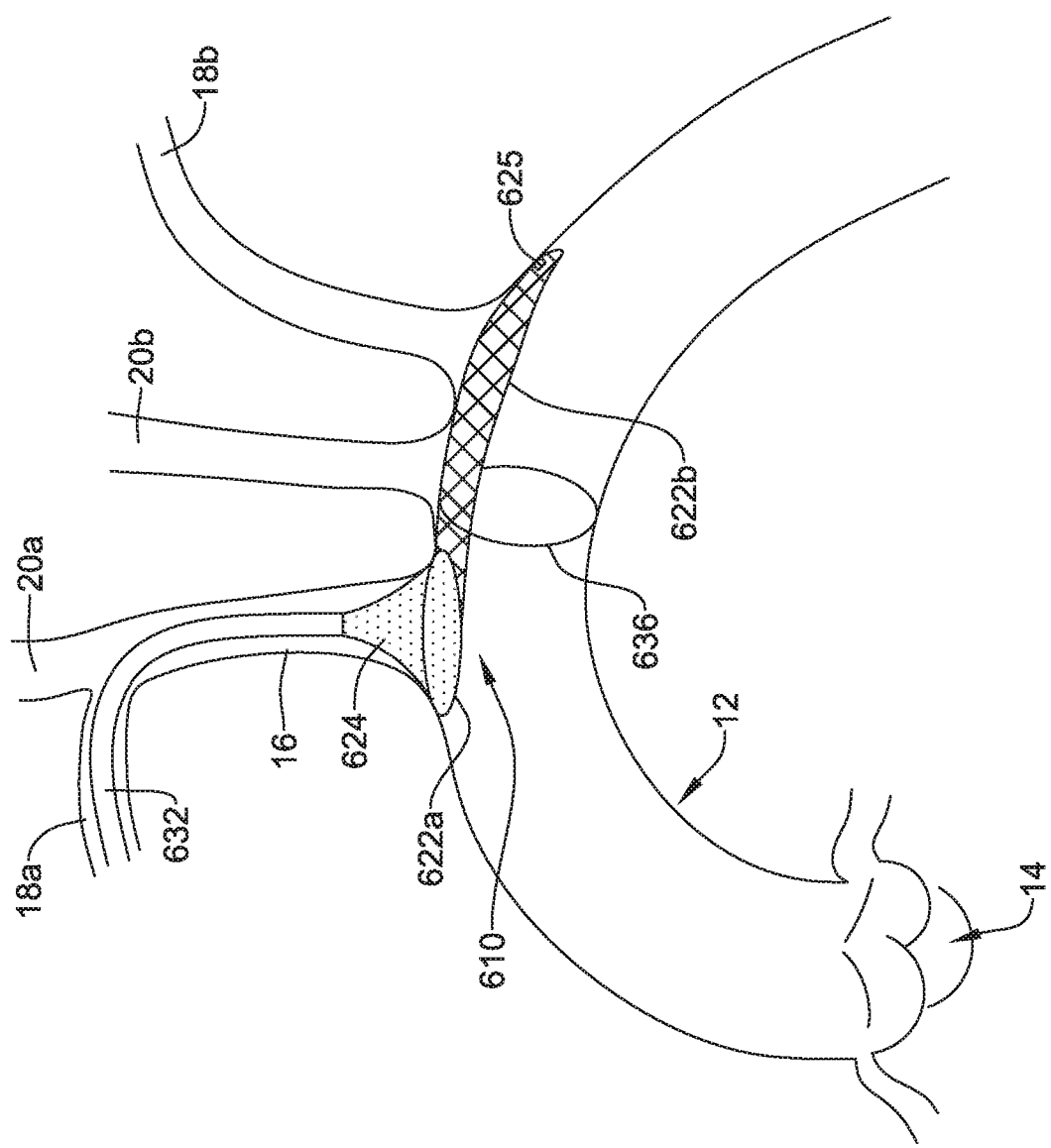
FIG. 10 is a plan view of an example embolic protection device disposed in a blood vessel.

FIG. 10 depicts another example embolic protection device 610, which may be similar in form and function to other embolic protection devices disclosed herein. The embolic protection device 610 may include a first stent or anchor 622*a* and a second stent or anchor 622*b*. A membrane 624 may be coupled to the first anchor 622*a*. The membrane 624 may be permeable to blood (e.g., which may include cells, blood components, and the like) while being resistant to the passing of embolic material.

The embolic protection device 610 may include a support hoop 636. The support hoop 636 may be designed to help anchor the embolic protection device 610 in place. In some instances, the support hoop 636 is designed to extend about the interior of the aorta 12. The support hoop 636 may be self-expanding (e.g., the support hoop may be formed from a nickel-titanium alloy such as nitinol) and exert a force upon the aorta 12 in order to help anchor the embolic protection device 610.

Like the other embolic protection devices disclosed herein, the embolic protection device 610 may include one more features that allow the device 610 to be imaged in a surgical suite and/or in an environment where fluoroscopic imaging equipment is not always present. For example, in some instances, the embolic protection device 610 may include a radiopaque material, an ultrasound-sensitive coating or material, or the like. In some of these and in other instances, the embolic protection device 610 may include a sensor 625. In FIG. 10, the sensor 625 is schematically depicted and the sensor 625 may be a part of or incorporated into the anchor 622*a*/622*b*, the sensor 625 may be a part of or incorporated into the membrane 624*a*/624*b*, and/or combinations thereof. In general, the sensor 625 may be used to help identify the location of the embolic protection device 610 during and after delivery. The sensor 625 may be compatible with one or more pieces of imaging hardware such as those typically found in a surgical suite. In some instances, the sensor 625 may be an impedance sensor, a flow sensor, a pressure sensor, or the like.

Also shown in FIG. 10 is a delivery member 632. In this example, the delivery member 632 takes the form of a delivery catheter coupled to the embolic protection device 610. The delivery member 632 may be used to help deliver/position the embolic protection device 610. For example, the delivery member 632 may be used to help navigate the embolic protection device 610 through the right subclavian artery 18*a*, through the brachiocephalic trunk 16, and into the aorta 12. In at least some instances, a filter wire (not shown) may be coupled to the embolic protection device 610 and may extend through the delivery member 632 during delivery.

The first anchor 622*a* of the embolic protection device 610 may form or otherwise resemble a bumper (e.g., similar to the bumper 434). In at least some instances, the first anchor/bumper 622*a* may be designed to provide a tactile feedback to a clinician during delivery of the embolic protection device 610. For example, the embolic protection device 610 may be advanced into the aorta 12. When doing so, the first anchor/bumper 622*a* may also be advanced within the aorta 12. In some instances, the first anchor/bumper 622*a* may be in a first or collapsed configuration when advancing into the aorta 12 and then may shift to an expanded configuration when reaching the aorta 12. When a clinician determines that the embolic protection device 610 is suitably positioned within the aorta 12, the clinician may exert a proximally-directed force onto the filter wire 632. When doing so, the first anchor/bumper 622*a* may lodged against the ostium of the brachiocephalic trunk 16 and be resistant to being moved further proximally. The resistance may provide a tactile feedback (e.g., a feeling that the first anchor/bumper 622*a* is securely lodged against the anatomy) to the clinician that indicates that the embolic protection device 610 is suitably delivered to a desirable location.

Figure 11:
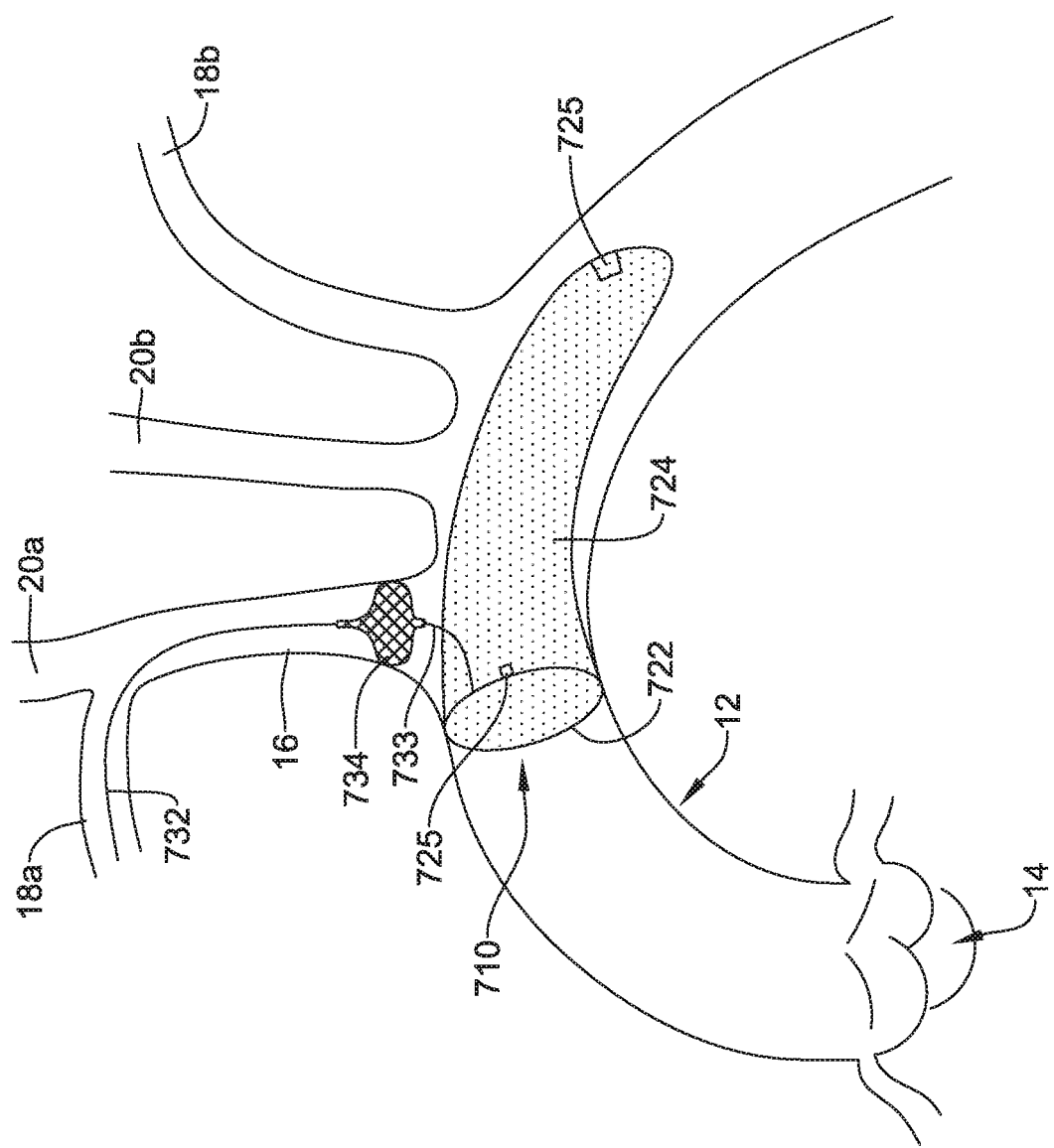
FIG. 11 is a side view of a portion of an example embolic protection device.

FIG. 11 depicts another example embolic protection device 710, which may be similar in form and function to other embolic protection devices disclosed herein. The embolic protection device 710 may include a stent or anchor 722. A membrane 724 may be disposed along the anchor 722. The membrane 724 may be permeable to blood (e.g., which may include cells, blood components, and the like) while being resistant to the passing of embolic material. In the embolic protection device 710, the anchor 722 may take the form of a loop that can be used anchor the embolic protection device 710 at a suitable location (e.g., upstream of the brachiocephalic trunk 16, right subclavian artery 18*a*, left subclavian artery 18*b*, right common carotid artery 20*a*, and/or left common carotid artery 20*b*) and the membrane 724 may take the form of a sac (e.g., which may resemble a windsock) that is secured to the anchor 722 and extends upstream therefrom.

Like the other embolic protection devices disclosed herein, the embolic protection device 710 may include one more features that allow the device 710 to be imaged in a surgical suite and/or in an environment where fluoroscopic imaging equipment is not always present. For example, in some instances, the embolic protection device 710 may include a radiopaque material, an ultrasound-sensitive coating or material, or the like. In some of these and in other instances, the embolic protection device 710 may include a sensor 725. In FIG. 11, the sensor(s) 725 are schematically depicted and the sensor 725 may be a part of or incorporated into the anchor 722, the sensor 725 may be a part of or incorporated into the membrane 724, and/or combinations thereof. In general, the sensor 725 may be used to help identify the location of the embolic protection device 710 during and after delivery. The sensor 725 may be compatible with one or more pieces of imaging hardware such as those typically found in a surgical suite. In some instances, the sensor 725 may be an impedance sensor, a flow sensor, a pressure sensor, or the like.

Also shown in FIG. 11 is a delivery member 732. In this example, the delivery member 732 takes the form of a filter wire coupled to the embolic protection device 710. The delivery member 732 may be used to help deliver/position the embolic protection device 710. For example, the delivery member 732 may be used to help navigate the embolic protection device 710 through the right subclavian artery 18a, through the brachiocephalic trunk 16, and into the aorta 12. This may include passing the delivery member 732 (and the embolic protection device 710) through a delivery catheter (not shown).

The embolic protection device 710 may include a bumper 734. A shaft 733 may extend between the bumper 734 and the anchor 722. In this example, the bumper 734 takes the form of a woven disk. In at least some instances, the bumper 734 may be designed to shift between a first or collapsed configuration and a second or expanded configuration. In FIG. 11, the bumper 734 is depicted in an example "expanded" configuration. In at least some instances, the bumper 734 may be designed to provide a tactile feedback to a clinician during delivery of the embolic protection device 710. For example, the embolic protection device 710 may be advanced into the aorta 12. When doing so, the bumper 734 may also be advanced within the aorta 12. In some instances, the bumper 734 may be in the first configuration when advancing into the aorta 12 and then may shift to the expanded configuration when reaching the aorta 12. When a clinician determines that the embolic protection device 710 is suitably positioned within the aorta 12, the clinician may exert a proximally-directed force onto the filter wire 732. When doing so, the bumper 734 may lodged against the ostium of the brachiocephalic trunk 16 and be resistant to being moved further proximally. The resistance may provide a tactile feedback (e.g., a feeling that the bumper 734 is securely lodged against the anatomy) to the clinician that indicates that the embolic protection device 710 is suitably delivered to a desirable location.

Figure 12:
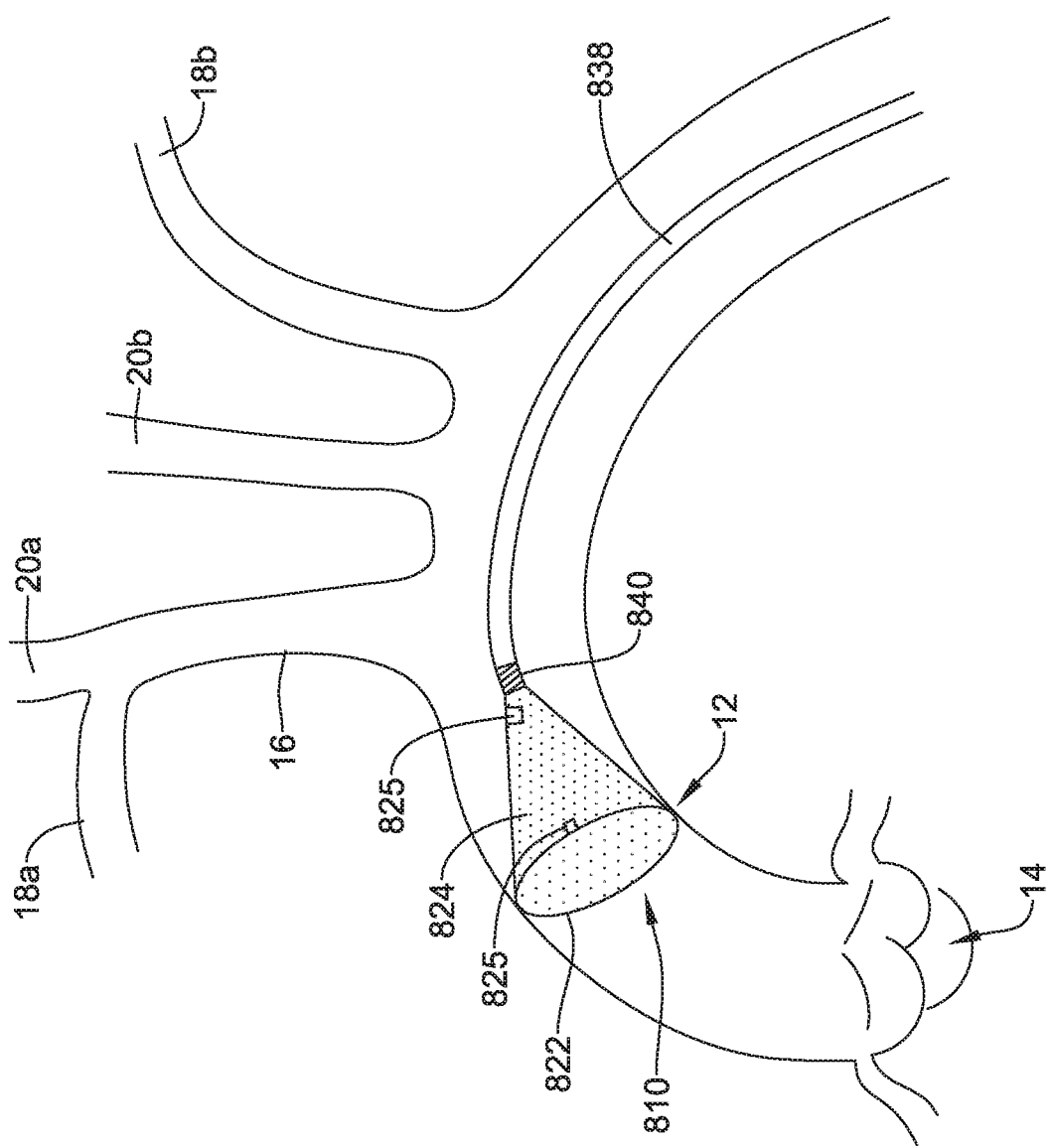
FIG. 12 is a plan view of an example embolic protection device disposed in a blood vessel.

FIG. 12 is a plan view of another example embolic protection device 810, similar in form and function to other embolic protection devices disclosed herein. The embolic protection device 810 may include a stent or anchor 822. A membrane 824 may be coupled to the anchor 822. The embolic protection device 810 may include a sensor 825. The embolic protection device 810 may be delivered using a delivery catheter 838. The delivery catheter 838 may be joined to the anchor 822 by a connector 840. In this example, the connector 840 is a detachable connector 840 (e.g., a threaded connector).

The materials that can be used for the various components of the embolic protection device 10 (and/or other embolic protection devices disclosed herein) may include those commonly associated with medical devices. For simplicity purposes, the following discussion makes reference to the anchor 22 and other components of the embolic protection device 10. However, this is not intended to limit the devices and methods described herein, as the discussion may be applied to other similar structure or devices as disclosed herein.

The anchor 22 and/or other components of the embolic protection device 10 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the embolic protection device 10 may also be doped with, made of, or otherwise include a radiopaque material. Radiopaque materials are understood to be materials capable of producing a relatively bright image on a fluoroscopy screen (e.g., where the bright image appears as a dark mark on the fluoroscopy screen) or another imaging technique during a medical procedure. This relatively bright image aids the user of the embolic protection device 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the embolic protection device 10 to achieve the same result.

In some embodiments, a degree of Magnetic Resonance Imaging (MRI) compatibility is imparted into the embolic protection device 10. For example, the embolic protection device 10, or portions thereof, may be made of a material that does not substantially distort the image and create substantial artifacts (e.g., gaps in the image). Certain ferromagnetic materials, for example, may not be suitable because they may create artifacts in an MRI image. The embolic protection device 10, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. An embolic protection device, comprising:
an elongate filter wire having a distal end region;
a filter anchor coupled to the distal end region;
a filter membrane coupled to the filter anchor; and
a bumper coupled to the filter anchor, the bumper being configured to engage the wall of a blood vessel and to provide a tactile feedback to a clinician during delivery of the embolic protection device, wherein the bumper includes a woven disk.

2. The embolic protection device of claim 1, wherein the filter anchor includes a hoop.

3. The embolic protection device of claim 1, wherein the filter anchor includes a stent-like structure.

4. The embolic protection device of claim 1, wherein the filter membrane includes a mesh.

5. The embolic protection device of claim 1, wherein the filter membrane includes a sac.

6. The embolic protection device of claim 1, further comprising an ultrasound-visible coating disposed along at least a portion of the filter wire, the filter anchor, the filter membrane, the bumper, or combinations thereof.

7. The embolic protection device of claim 1, further comprising a sensor coupled to at least one of the filter wire, the filter anchor, the filter membrane, or the bumper.

8. The embolic protection device of claim 7, wherein the sensor includes an impedance sensor.

9. The embolic protection device of claim 7, wherein the sensor includes a flow sensor.

10. The embolic protection device of claim 7, wherein the sensor includes a pressure sensor.

* * * * *